US007738959B2

(12) United States Patent
Manrodt et al.

(10) Patent No.: US 7,738,959 B2
(45) Date of Patent: Jun. 15, 2010

(54) METHOD AND APPARATUS FOR PERFORMING STIMULATION THRESHOLD SEARCHES

(75) Inventors: Christopher M. Manrodt, White Bear Lake, MN (US); Todd J. Sheldon, North Oaks, MN (US); Bradley C. Peck, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 1860 days.

(21) Appl. No.: 10/260,984

(22) Filed: Sep. 30, 2002

(65) Prior Publication Data

US 2004/0064162 A1 Apr. 1, 2004

(51) Int. Cl.
*A61N 1/37* (2006.01)
(52) U.S. Cl. ........................................ 607/28
(58) Field of Classification Search .................. 607/28, 607/14
See application file for complete search history.

(56) References Cited

U.S. PATENT DOCUMENTS

| 4,114,627 A | 9/1978 | Lewyn et al. ................ 128/419 |
| 4,444,144 A | 4/1984 | Kopilak ........................ 114/114 |
| 4,549,548 A | 10/1985 | Wittkampf et al. ........... 128/419 |
| 5,003,975 A | 4/1991 | Hafelfinger et al. ... 128/419 PG |
| 5,172,690 A | 12/1992 | Nappholz et al. ............ 128/419 |
| 5,306,292 A | 4/1994 | Lindegren .................... 607/11 |
| 5,350,410 A | 9/1994 | Kleks et al. ................... 607/28 |
| 5,431,693 A | 7/1995 | Schroeppel .................. 607/28 |
| 5,571,144 A | 11/1996 | Schroeppel .................. 607/28 |
| 5,902,325 A | 5/1999 | Condie et al. ................ 607/28 |
| 6,134,473 A | 10/2000 | Hemming et al. ............ 607/28 |
| 6,144,881 A | 11/2000 | Hemming et al. ............ 607/28 |
| 6,456,878 B1 | 9/2002 | Yerich et al. .................. 607/9 |
| 6,546,288 B1* | 4/2003 | Levine ........................ 607/28 |
| 6,549,806 B1* | 4/2003 | Kroll ........................... 607/27 |
| 6,611,712 B2* | 8/2003 | Spinelli et al. ............... 607/11 |
| 6,782,291 B1* | 8/2004 | Bornzin et al. ............... 607/28 |
| 6,978,178 B2* | 12/2005 | Sommer et al. .............. 607/28 |
| 7,020,523 B1* | 3/2006 | Lu et al. ...................... 607/27 |
| 2002/0078968 A1 | 6/2002 | Spinelli et al. ............. 128/906 |

* cited by examiner

*Primary Examiner*—George R Evanisko
*Assistant Examiner*—Amanda Patton
(74) *Attorney, Agent, or Firm*—Stephen W. Bauer

(57) ABSTRACT

Undersensing of an evoked response during an automatically initiated search of the stimulation threshold in a stimulation channel of an IMD, e.g., the pacing threshold in a pacing channel of a pacing system, is minimized by repeating the search using the sense amplifier of the stimulation channel configured in bipolar and unipolar sensing configurations. A failure to sense an evoked response in the search in one sensing configuration can be confirmed, and stimulation energy set to a high output, if an evoked response is not sensed in an alternate sensing configuration or refuted if an evoked response is sensed in the alternate sensing configuration. If the failure is refuted, the alternate sensing configuration is employed until the next search.

8 Claims, 5 Drawing Sheets

Low Polarization Example

High Polarization Example

METHOD AND APPARATUS FOR PERFORMING STIMULATION THRESHOLD SEARCHES

FIELD OF THE INVENTION

This invention relates generally to the field of implantable medical devices (IMDs), and more particularly relates to implantable pulse generators (IPGs) that provide electrical stimulation to body tissue, periodically determine the stimulation threshold level sufficient to evoke a tissue response, and an improved response to a determination that the stimulation threshold level is unacceptably high.

BACKGROUND OF THE INVENTION

At present, a wide variety of IMDs are commercially released or proposed for clinical implantation that are programmable in a variety of operating modes and are interrogatable using RF telemetry transmissions. Such IMDs include implantable cardiac pacemakers, cardioverter/defibrillators, cardiomyostimulators, pacemaker/cardioverter/defibrillators, drug delivery systems, cardiac and other physiologic monitors, electrical stimulators including nerve and muscle stimulators, deep brain stimulators, cochlear implants, and heart assist devices or pumps, etc.

Most such IMDs comprise electronic circuitry and an IMD battery that provides power to the electronic circuitry and that depletes in energy over time. Therefore, it is necessary to monitor the state of the battery in such IMDs so that the IMD can be replaced before the battery depletes to a state that renders the IMD inoperable. Moreover, such IMDs that deliver energy to tissue deplete a discrete bolus of battery energy with each delivery typically change operating mode and provide a signal when battery energy depletes to a level that precedes and predicts battery end of life.

Since it is often extremely critical for patients' well-being that IMDs do not cease operating, it is common for IMDs to monitor the level of battery depletion and to provide some indication when the depletion reaches a level at which the battery should be replaced.

Single chamber, dual chamber and right and left heart cardiac pacemaker IPGs and certain implantable cardioverter/defibrillators (ICDs) having a pacing function (herein pacing IPGs) deliver pacing pulses through pacing leads to unipolar or bipolar electrodes disposed about the heart to evoke a depolarization of a heart chamber to establish or regulate the heart rate and rhythm of the heart chambers, typically in a rate response mode wherein the rate is dependent on sensed need for cardiac output. Atrial and ventricular pacing IPGs typically have separate sense amplifiers for atrial and/or ventricular sensing coupled to unipolar or bipolar electrode pairs through atrial and/or ventricular leads. Atrial sense amplifiers detect the presence of intrinsic atrial cardiac depolarization signals, particularly the P-wave, through such unipolar or bipolar electrode pairs and generate an atrial sense event. Ventricular sense amplifiers detect the presence of intrinsic ventricular cardiac depolarization signals, particularly the R-wave, through such unipolar or bipolar electrode pairs and generate a ventricular sense event. Timing and control circuitry and operating algorithms respond to such atrial and/or ventricular sense events to restart a pacing escape interval being timed out that effectively inhibits the delivery of a pacing pulse to the corresponding chamber.

Thus, such pacing IPGs typically operate in a defined or programmed pacing mode to pace and sense in programmed pacing channels, and each delivered pacing pulse consumes battery energy. Typically, the operating system monitors battery energy and depletion and develops an "elective replacement indicator" (ERI) when the battery depletion reaches a level such that replacement will soon be needed to avoid further depletion to a battery "end of life" (EOL) condition. Operating circuitry in the pacing IPG typically responds to issuance of an ERI by switching or deactivating operating modes to lower power consumption in order to maximize the ERI-to-EOL interval. For example, internal diagnostic functions and advanced rate-response functions may be discontinued upon issuance of ERI. Moreover, the battery impedance, voltage and other indicators of the level of battery depletion can be interrogated during a telemetry session and uplink telemetry transmitted for display and analysis employing the programmer as described above.

In addition, the minimum pacing pulse energy that evokes a depolarization or "captures" the heart and the pacing pulse energy level at which loss of capture (LOC) occurs is determined upon initial implantation of the pacing IPG and leads. The physician programs the initial pacing pulse energy (pulse width and/or amplitude) to an energy level exceeding the LOC energy level and providing a "safety margin". Thus, the pacing pulse energy can be programmed to safely minimize the power consumption to prolong battery life. This testing and programming of the pacing pulse energy level is conducted for each atrial and/or ventricular pacing channel employing an external programmer and telemetry system to sequentially adjust the pacing pulse energy as well as external equipment that can verify that the delivered pacing pulse at the programmed energy has or has not captured the heart.

Many current pacing IPGs also periodically enter a test mode to automatically determine the stimulation threshold employing the sense amplifier of the pacing channel to detect the evoked response. In certain cases, the LOC energy level is determined, and the pacing pulse energy is automatically adjusted to a level providing the safety margin to conserve battery energy. Detection of changes in the stimulation threshold may also be useful for ascertaining the physiological effect of drugs or for diagnosing abnormal cardiac conditions. However, it is more difficult to employ the sense amplifier coupled to the pace/sense electrodes to detect an evoked response or absence of an evoked response for a number of reasons.

First of all, if an evoked response occurs, it does so a short time after delivery of the pacing pulse. But, the sense amplifiers of the pacing channels must be "blanked" during delivery of the pacing pulses to the pacing channels so that the pacing pulse energy does not damage the sense amplifier circuitry. The evoked response may not be sensed if the sense amplifier is blanked for too long a time after the delivery of the pacing pulse.

Secondly, the generation and delivery of a pacing pulse gives rise to the storage of charge in body tissues at the electrode-tissue interface. Such stimulation polarization artifacts or signals, referred to as "after potentials" or "repolarization signals", typically have much larger amplitudes than those arising from an intrinsic heartbeat. And, if the pacing pulse causes an evoked response in the cardiac tissue, then the evoked response is itself superimposed atop the typically much larger amplitude polarization signal. As a result, conventional pacing IPGs either cannot differentiate, or have difficulty differentiating, between polarization signals and evoked response signals. This problem is further complicated and exacerbated by the fact that residual polarization signals typically have high amplitudes even when evoked response signals do occur. Consequently, it becomes difficult, if not impossible to detect an evoked response using a conventional sense amplifier that uses linear frequency filtering techniques. As a result, most pacing IPGs have great difficulty differentiating between polarization and evoked response signals.

Thus, most pacing IPGs employ sensing and timing circuits that attempt to detect evoked response signals only when the polarization signal is no longer present or has subsided to some minimal amplitude level. Only then is sensing considered reliable. In respect to capture detection methods, however, such sensing may occur only after a significant period of time has elapsed. As a result, many pacing IPGs may not detect evoked response signals with any degree of confidence.

A unipolar pacing lead disposes a single active pace/sense electrode typically affixed at a site of a heart chamber or in a coronary vessel and employs the IPG conductive housing or "can" as a remote return of indifferent pace/sense electrode. A bipolar pacing lead disposes the active and indifferent pace/sense electrodes relatively closely spaced at the site. Typical bipolar leads support the active pace/sense electrode at the lead body distal end as a tip electrode and the indifferent pace/sense electrode proximally from the distal end as a ring electrode. There are typically two electrode-tissue interfaces in a pacing channel, one at the tip electrode, and one at the ring (or casing) electrode that store energy that dissipates after the pace event, creating the after-potential.

The impedance or load presented to the sense amplifier in the pacing channel comprises the impedance of the lead itself, the electrode-tissue interface impedances, and the impedance of the body tissue bulk. The impedances of the body tissue and the lead may be modeled as a simple series resistance, leaving the electrode-tissue interfaces as the reactive energy absorbing/discharging elements of the total load. The tip electrode is the primary after-potential storage element in comparison to the IPG can and ring electrodes. In a pacing channel, a ring electrode typically stores more energy than does an IPG can electrode because the surface area of the ring electrode is smaller that the surface area of the IPG can electrode.

Several methods have been proposed in the prior art for improving the ability of a pacing IPG sense amplifier to detect and measure evoked responses.

For example, U.S. Pat. No. 5,172,690 to Nappholz et al., proposes a tri-phasic stimulation waveform consisting of pre-charge, stimulus, and post-charge segments. The duration of the precharge segment is varied until the amplitude of the stimulation artifact is smaller than the evoked response.

U.S. Pat. No. 5,431,693 to Schroeppel discloses a pacemaker that low-pass filters a sensed signal to remove noise and passes frequencies characteristic of the evoked cardiac signal. The filtered signal is processed to render a waveform signal representing the second derivative of the filtered signal. The second derivative filtered signal is further analyzed to detect minimum and maximum amplitude excursions during selected first and second time windows. The amplitude differences measured during the two time windows are compared to one another to determine whether capture has occurred.

U.S. Pat. No. 5,571,144 to Schroeppel discloses a capture detection system involving analysis of post-stimulus signal morphology.

U.S. Pat. No. 4,114,627 to Lewyn et al. discloses pacing circuitry that delivers pacing pulses through an output coupling capacitor. During delivery of a pacing pulse, the sense amplifier is uncoupled from the cardiac electrode. When the pacing pulse terminates, the output coupling capacitor is coupled to ground through a discharge resistor, thereby discharging electrode polarization.

German Patent No. 4,444,144 to Hauptmann discloses a pacemaker having a sensing circuit that records intracardiac heart signals. An adaptive non-linear noise filter transforms those signals. A matched filter correlates the transformed signals to a pulse pattern and creates an output indicative of heart signals. The sensing circuit reduces faulty signal detection caused by noise filtering by permitting external noise to be distinguished from noise associated with true heart signals.

U.S. Pat. No. 4,549,548 to Wittkampf et al. describes a system whereby the polarity of the lead can switch automatically between unipolar and bipolar configurations to optimize pacing and sensing operations. In one mode, the system employs bipolar QRS sensing and unipolar pacing and T-wave sensing. In another mode, the system employs bipolar QRS sensing and pacing, and unipolar T-wave sensing.

U.S. Pat. No. 5,306,292 to Lindegren describes an auto-capture system that automatically tests a number of conductive surfaces to provide the lowest stimulation threshold. In order to reduce the energy consumption, an autocapture unit is provided which automatically tests a number of possible combinations of conductive surfaces for stimulation and selects the combination providing the lowest stimulation threshold for connection to the pulse generator.

U.S. Pat. No. 5,350,410 to Kleks et al. discloses an auto-capture system in which one embodiment tests all electrode combinations available to determine the optimum sensing configuration. The electrical post-stimulus signal of the heart following delivery of a stimulation pulse is compared to a polarization template, determined during a capture verification test. A prescribed difference between the polarization template and the post-stimulus signal indicates capture has occurred. Otherwise, LOC is presumed, and a loss-of-P-capture routine is invoked that increases the energy a prescribed amount to obtain capture.

U.S. Pat. No. 5,902,325 to Condie et al. describes a method of using cardiac impedance waveforms to determine cardiac capture resulting from pacing. Circuitry is provided in a pacemaker for obtaining a signal reflecting cardiac impedance, which is known to reliably reflect certain aspects of cardiac function. Circuitry is also provided for monitoring the cardiac impedance waveform during a predetermined capture detect window following delivery of pacing pulses. In one embodiment, the control values against which impedance waveform characterization values are compared are obtained by delivering a series of stimulation pulses having sufficient energy to ensure that capture is achieved, and by monitoring the impedance waveform during delivery of these pulses.

U.S. Pat. Nos. 6,134,473 and 6,144,881, both issued to Hemming et al., describe the Capture Management algorithm implemented, for example, in the Medtronic® Kappa® 700 pacemaker IPGs. The polarity of the positive or negative change in voltage with respect to time (or dv/dt) of the waveform incident on the lead electrodes is monitored during a short period of time immediately following a paced event. In one embodiment, sensing of the evoked response is based upon a relationship between a maximum magnitude of a derivative of a sensed signal and a predetermined threshold reference value. The evoked response is declared when the maximum amplitude of the derivative of the sensed signal equals or exceeds the threshold reference value.

The Capture Management algorithm is periodically run, e.g., once a day at a prescribed time to perform a pacing threshold search (PTS) wherein the pacing pulse amplitudes and pulse widths of the pacing pulses delivered in each pacing channel are incrementally adjusted within a predetermined range to determine the pacing threshold, and the threshold data is stored for analysis of long term trends. When an "Adaptive" mode of the Capture Management algorithm is programmed, the Capture Management algorithm automatically adjusts the pacing pulse amplitude and/or pulse width setting to ensure capture at minimum pacing energy while maintaining the programmed safety margin(s).

The Capture Management PTS was tested in pacing systems configured for bipolar pacing and sensing employing bipolar leads (bipolar polarity) and systems configured for unipolar pacing and sensing employing unipolar leads (unipolar polarity), and the resulting data were presented in Table 3 of the above-referenced '881 patent. The data shows further that capture detection accuracy was enhanced when tip-to-can (herein, the unipolar sense vector) sensing configurations were employed instead of tip-to-ring (herein, the bipolar sense vector) sensing configurations were employed, regardless of pacing pulse polarity.

Bipolar pacing and ICD leads that use short tip-to-ring spacing tend to be more susceptible to evoked response undersensing. In a bipolar pacing and sensing configuration, the evoked response signal occurs sooner after a delivery of a pacing pulse and is more likely to fall within the post-pace blanking period of the sense amplifier due to the relatively short tip-to-ring spacing. In a unipolar pacing and sensing configuration, the tip-to-can spacing is wide, and the occurrence of the evoked response takes place later in time after the pacing pulse is delivered than it does when delivered between the bipolar tip and can electrodes. It has also been observed in practice that Capture Management, as implemented in the Medtronic® Kappa® 700 pacemaker IPGs, occasionally displayed incidents of undersensing of a ventricular evoked response during a PTS leading to a mistaken declaration of a "high output" alert to inform the physician that intervention is necessary. Undersensing of an evoked response was determined to be due to low signal levels present in the programmed sensing configuration. Such undersensing has caused the IPG algorithm to respond by automatically setting the pacing pulse width and amplitude to their maximum programmable values. This false negative response has unnecessarily imposed excessive current drain on the battery and shortened battery life in affected pacing IPGs. Physicians have noted this during patient follow-up and have been able to reprogram the pacing pulse energy and sensing configuration to reduce the likelihood of recurrence. Reprogramming from the bipolar configuration to a unipolar configuration usually resolves the issue when undersensing occurs in the bipolar sensing polarity.

In spite of these advances, improvements are needed in the ability to reliably and consistently detect the evoked response during performance of a PTS and accurately adjust the pacing pulse energy only when necessary.

SUMMARY OF THE INVENTION

The present invention is designed to minimize undersensing of such an evoked response during a PTS initiated by the Capture Management algorithm or function.

The PTS is conducted in each pacing channel in a predetermined sequence to test whether or not an evoked response to the pacing pulse delivered in the same channel can be detected by the sense amplifier of the pacing channel. It should be noted that delivery of the pacing pulse in the pacing can be programmed to be delivered in a bipolar pace mode between the tip electrode and the ring electrode on a bipolar lead or in a unipolar pace mode between the active tip electrode and the remote can electrode or any other indifferent electrode of another lead coupled to the pacing IPG. Similarly, the sense amplifier inputs of the pacing channel can be programmed to sense in a unipolar sense vector or the bipolar sense vector of the pacing channel. Thus, pacing can be performed in one of the unipolar and bipolar pace vectors and sensing can be performed in the same or the other of the unipolar and bipolar sense vectors of the channel.

In accordance with the present invention, the sense amplifier sense vector is changed by the Capture Management algorithm of the present invention to a different available sense vector and the PTS is repeated if the initial PTS results in a failure to sense an evoked response at an acceptable pulse energy. For example, a switch network is operated to change the sense vector from the prevailing bipolar sense vector to a unipolar sense vector or from the prevailing unipolar sense vector to the bipolar sense vector of the pacing channel. The pace vector of the pacing channel is unchanged, and the PTS is then repeated.

If the second (or further) PTS results in a failure to sense an evoked response, then the "high output" alert is confirmed and stored in memory with a date stamp and other data to be retrieved in a subsequent patient follow-up. The pacing pulse energy of pacing pulses delivered in the pacing channel is set to the maximum or high output level.

But, the "high output" alert is revoked or refuted if an evoked response is detected during the second PTS at a pacing energy level that allows the acceptable safety margin to be provided. Pacing and sensing then continue in that channel at the new pacing pulse energy and in the changed sense vector until the Capture Management algorithm is invoked again, typically 24 hours later. In this way, undersensing errors are reduced, and battery energy is conserved.

When the Capture Management algorithm is next invoked, it commences with the current prevailing sense vector. Each change in pacing pulse energy and each change in sense vector are recorded with a date stamp.

Typically, it would be expected that the undersensing would occur when sensing in the bipolar sense vector of the channel, and that switching to the unipolar sense vector would negate such undersensing. Conversely, a "high output" declared when conducting the PTS while sensing in the bipolar sense vector can be verified if it is also declared when conducting the PTS while sensing in the unipolar sense vector.

Furthermore, when detecting the presence of an evoked response, the sense amplifier can actually measure the amplitude of the evoked response rather than simply determine whether the evoked response has crossed a certain programmed threshold. This capability allows the sense amplifier to select the signal that has the highest signal to noise ratio-usually the evoked response. Such measurements are possible because the sense amplifier can also switch to various available sense vectors to settle on the best one to measure the amplitude of the evoked response. This capability offers an alternate method to avoid undersensing.

In a further variation the sensing configurations can be selected and programmed for use by the sense amplifier of the channel among all possible vectors available to the IPG to resolve which sense vector is best able to measure the evoked response when noise is present in other sense vector(s). Such sense vectors include those between tip-to-ring (on the same lead), tip-to-can, can-to-tip, tip-to-ring (between two leads), tip-to-tip and ring-to-ring (between two leads), among others. These latter vectors may be advantageously used in ICDs and right and left heart pacing systems for CHF patients, among others, which use multiple leads for various operations in which it is necessary to know both whether an evoked response is present as well as the amplitude of such a response. A similar advantage is applicable for lead(s) that may be positioned in non-traditional sites, such as in the ventricular outflow tract, on the septal wall, or in left-sided stimulation, among others. The same advantages apply equally to leads with short tip-to-ring spacing and other non-traditional electrode positioning.

Briefly stated, there are two ways in which the PTS can result in undersensing the evoked response. First, lead polarization or background noise level is too high thereby making it difficult to sense the evoked response. The cause of the problem is usually due to the use of a high polarization lead. Alternatively, the signal amplitude of the evoked response is too low. This situation is usually due to the use of a short tip-to-ring spaced lead, resulting in the evoked response occurring within the post-pace blanking period. The present invention overcomes both of these issues by switching from one sense vector to another, from a bipolar sense vector to a unipolar sense vector, and/or measuring the signal with the highest signal to noise ratio.

BRIEF DESCRIPTION OF THE DRAWINGS

These and other aspects and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS

In the following detailed description, references are made to a dual chamber pacing system operable in the DDD and DDDR pacing modes for restoring synchrony of the atria and ventricles as well as other programmable pacing modes in which the present invention can be implemented. It is understood that the present invention can be implemented in other pacing systems without departing from the scope of the invention. For example, the invention can be incorporated into an ICD having bradycardia pacing and high rate pacing and cardioversion shock therapies for providing staged therapies to treat a diagnosed cardiac arrhythmia. Moreover, the present invention can be implemented in bi-atrial and/or bi-ventricular pacing systems and ICDs for CHF.

Figure 1:
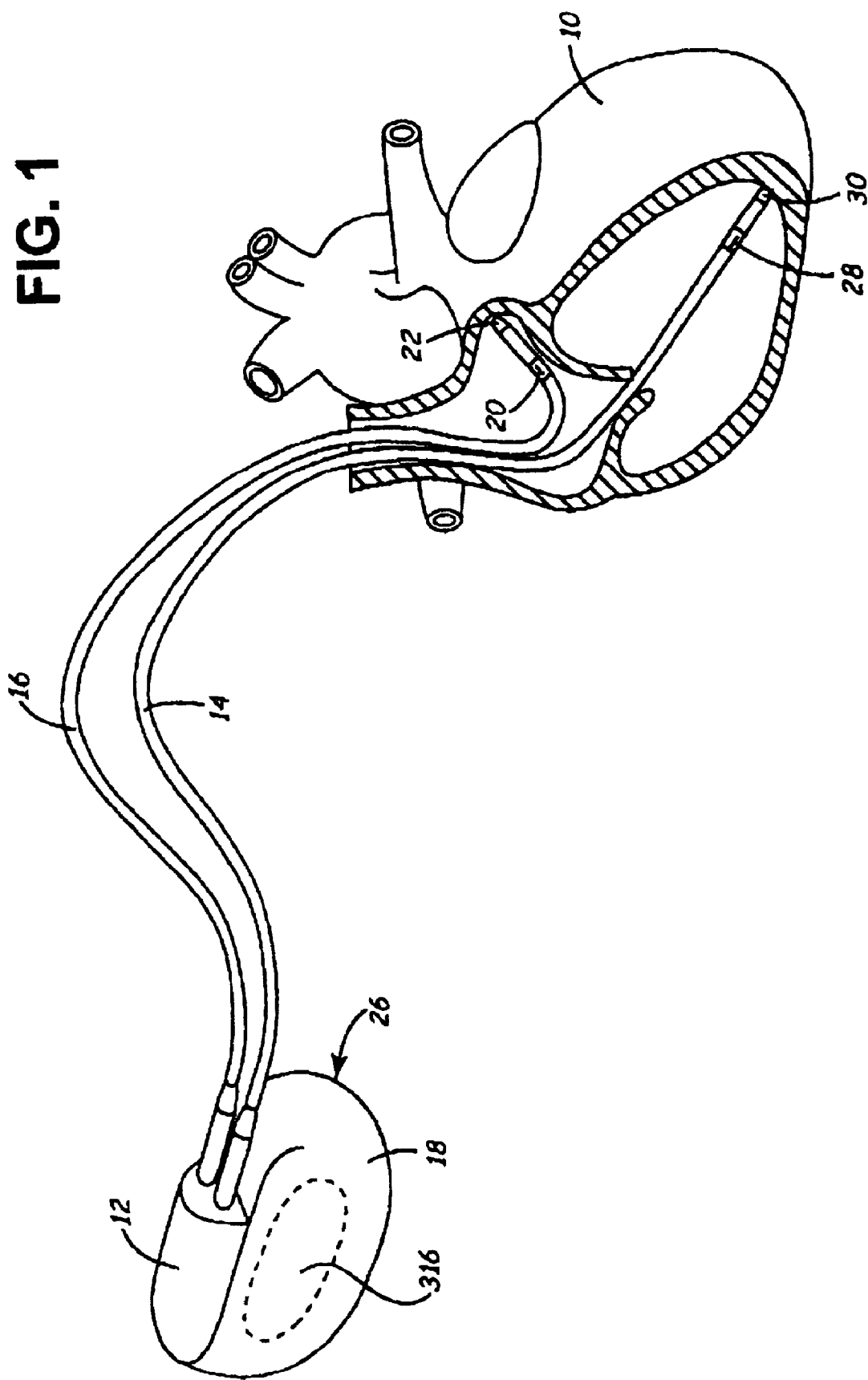
FIG. 1 is an illustration of an implantable dual chamber pacing IPG and set of cardiac pacing leads illustrated as located in a cutaway view of a human heart in which the present invention may be advantageously practiced.

FIG. 1 illustrates the external configuration of a dual chamber pacing IPG 26 coupled to atrial and ventricular bipolar endocardial leads 4 14 and 16 to form a dual chamber pacemaker. The pacing IPG 26 is formed having a hermetically sealed can or housing 18, typically fabricated of bio-compatible metal such as titanium enclosing the electronic circuitry and battery depicted in FIG. 2 and a connector block assembly or header 12 mounted to the housing 18. Header 12 is preferably formed of polyurethane or any other suitable bio-compatible material or metal. Header 12 comprises a pair of connector bores that receive the connector elements of the atrial and ventricular leads 14 and 16. Header 12 also encases one or more hermetic feedthrough elements (not shown) for conducting electrical signals of the heart and pacing pulses between the conductors of leads 14 and 16 and the electronic pacing circuitry disposed within can 18.

In this particular illustrated embodiment, a patient activity sensor 316 that takes the form of a piezoelectric crystal transducer is coupled to the interior surface of the IPG housing 18 as is well known in the art. Additional or other physiologic sensors of the need for cardiac output experienced by the patient during exercise and rest that are well known in the art can be incorporated into the IPG 26 and/or leads 14 and 16.

The IPG housing 18 can be employed as a remote indifferent pace/sense electrode referred to as the IND_CAN electrode. Atrial and ventricular sensing and pacing can be programmed in various unipolar and bipolar modes. Atrial and ventricular sensing can be switched as described herein during the Capture Management routine between bipolar and unipolar sensing modes along atrial bipolar and unipolar sense vectors, respectively.

Lead 16 is an bipolar atrial pacing lead, supporting ring and tip electrodes 20 and 22 that are used in a bipolar or unipolar sensing mode to sense atrial depolarizations (P-waves) and bipolar or unipolar pacing mode to deliver atrial pacing (A-PACE) pulses to the right atrium. A-PACE pulses are delivered between electrodes 20 and 22 in the bipolar pacing mode and between tip electrode 22 and the IND_CAN electrode in the unipolar pacing mode. Bipolar P-wave sensing takes place between electrodes 20 and 22 when the atrial sense amplifier is coupled to electrodes 20 and 22 in the bipolar sensing mode. Thus, the atrial bipolar sense vector is defined by a vector between electrodes 20 and 22. The atrial sense amplifier is typically coupled to one of electrodes 20 and 22 and the IND_CAN electrode in the unipolar sensing mode. However, the atrial sense amplifier can be coupled to one of pace/sense electrodes 20 and 22 and one of the ventricular lead pace/sense electrodes 28 and 30. Thus, the atrial unipolar sense vector is defined by a vector between the selected electrode 20 or 22 and the IND_CAN electrode or the selected electrode 28 or 30.

Similarly, lead 14 is a bipolar ventricular pacing lead, supporting ring and tip electrodes 28 and 30 that are used in a bipolar or unipolar sensing mode to sense ventricular depolarizations (R-waves) and bipolar or unipolar pacing mode to deliver ventricular pacing (V-PACE) pulses to the right ventricle. V-PACE pulses are delivered between electrodes 28 and 30 in the bipolar pacing mode and between tip electrode 30 and the IND_CAN electrode in the unipolar pacing mode. Bipolar R-wave sensing takes place between electrodes 28 and 30 when the ventricular sense amplifier is coupled to electrodes 28 and 30 in the bipolar sensing mode. Thus, the ventricular bipolar sense vector is defined by a vector between electrodes 28 and 30. The ventricular sense amplifier is typically coupled to one of electrodes 28 and 30 and the IND_CAN electrode in the unipolar sensing mode. However, the ventricular sense amplifier can be coupled to one of electrodes 28 and 30 and one of the atrial lead electrodes 20 and 22. Thus, the ventricular unipolar sense vector is defined by a vector between the selected electrode 28 or 30 and the IND_CAN electrode or the selected electrode 20 or 22.

Figure 2:
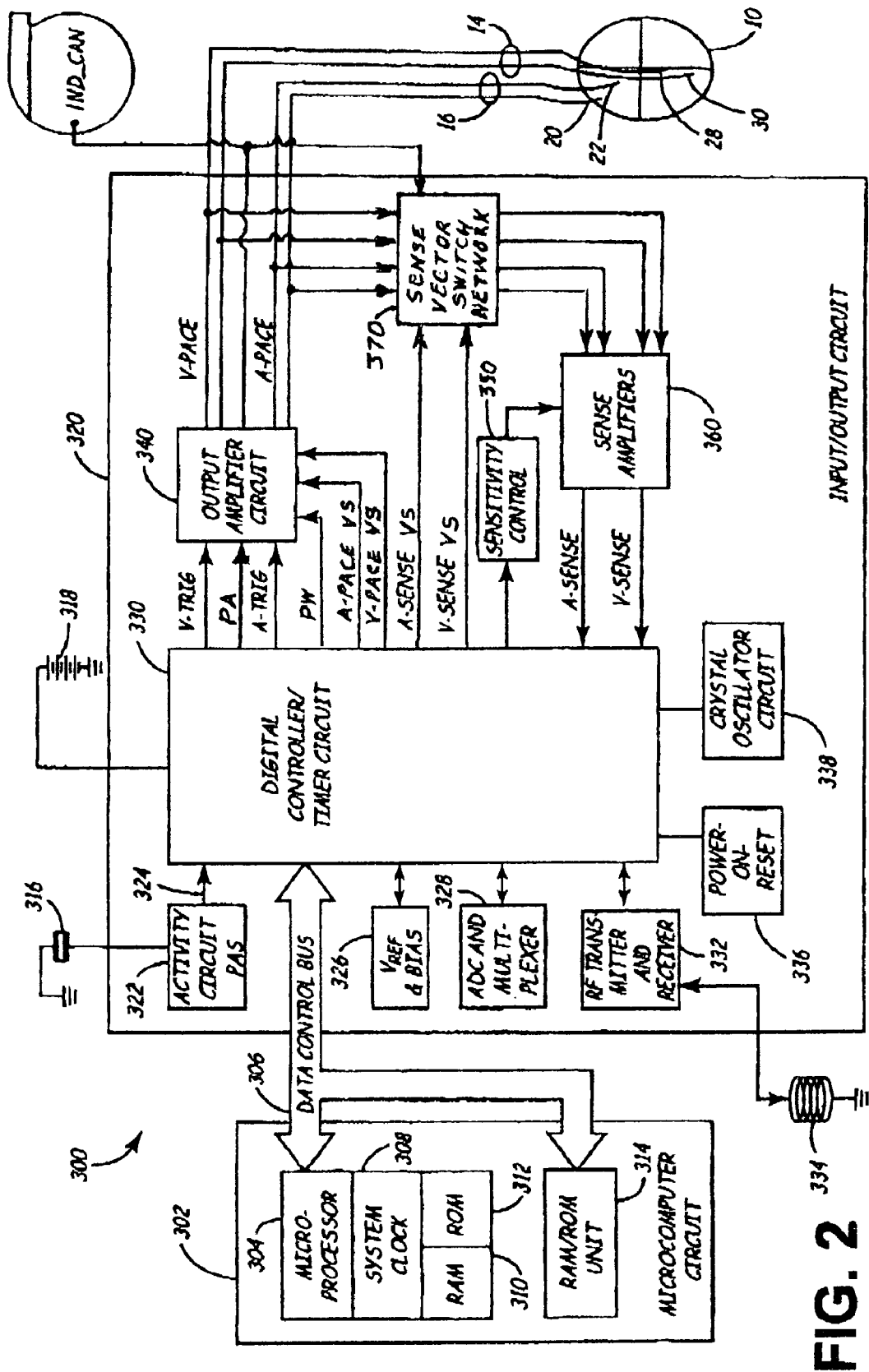
FIG. 2 is a block diagram of the circuitry of the dual chamber pacing IPG of FIG. 1 adapted to select atrial and ventricular sense vectors to confirm or refute a "high output" alert issued during a PTS in accordance with the present invention.

FIG. 2 depicts bipolar ventricular lead 14 and atrial lead 16 coupled with IPG circuit 300 having programmable modes and parameters and a telemetry transceiver having the components enabling operation in these modes with mode switching of a type known in the pacing art. The IPG circuit 300 is illustrated in a functional block diagram divided generally into a microcomputer circuit 302 and a pacing circuit 320. The pacing circuit 320 includes the digital controller/timer circuit 330, the output amplifiers circuit 340, and the sense amplifiers circuit 360, as well as a number of other circuits and components described below.

Crystal oscillator circuit 338 provides the basic timing clock for the pacing circuit 320, while battery 318 provides power. Power-on-reset circuit 336 responds to initial connection of the circuit to the battery for defining an initial operating condition and similarly, resets the operative state of the device in response to detection of a low battery condition. Reference mode circuit 326 generates stable voltage reference and currents for the analog circuits within the pacing circuit 320, while analog to digital converter ADC and multiplexer circuit 328 digitizes analog signals and voltage to provide real time telemetry if a cardiac signals from sense amplifiers 360, for uplink transmission via RF transmitter and receiver circuit 332. Voltage reference and bias circuit 326, ADC and multiplexer 328, power-on-reset circuit 336 and crystal oscillator circuit 338 may correspond to any of those presently used in current marketed implantable cardiac pacemakers.

Data transmission to and from the external programmer is accomplished by means of the telemetry antenna 334 and an associated RF transmitter and receiver 332, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and Marker Channel pulses indicating the occurrence of sensed and paced depolarizations in the atrium and ventricle, as are well known in the pacing art. In addition, a real time clock is incorporated into the digital controller/timer circuit for a number of uses, including timing the time of day when the PTS, e.g., pacing and sensing threshold tests, are to be undertaken or to append a date and time stamp to event data stored in memory for later telemetry out to an external programmer. In the context of the present invention, the occurrences of confirmed "high output" settings of the A-PACE or V-PACE pulses during the PTS is stored in memory with a date stamp for uplink telemetry in a telemetry session, so that the attending physician can intervene appropriately.

Microcomputer 302 contains a microprocessor 304 and associated system clock 308 and on-processor RAM and ROM chips 310 and 312, respectively. In addition, microcomputer circuit 302 includes a separate RAM/ROM chip 314 to provide additional memory capacity. Microprocessor 304 normally operates in a reduced power consumption mode and is interrupt driven. In one embodiment of the invention, microprocessor 304 is a custom microprocessor adapted to fetch and execute instructions stored in RAM/ROM unit 314 in a conventional manner. It is contemplated, however, that other implementations may be suitable to practice the present invention. For example, an off-the-shelf, commercially available microprocessor or micro controller, or custom application-specific, hardwired logic, or state-machine type circuit may perform the functions of microprocessor 304.

Microprocessor 304 is awakened in response to defined interrupt events, which may include A-TRIG and V-TRIG signals generated by timers in digital timer/controller circuit 330 and A-EVENT and V-EVENT signals generated by sense amplifiers circuit 360, among others. The specific values of the intervals and delays timed out by digital controller/timer circuit 330 are controlled by the microcomputer circuit 302 by means of data and control bus 306 from programmed-in parameter values and operating modes. Digital controller/timer circuit 330 includes a set of timing and associated logic circuits including discharge/recharge timers, an intrinsic interval timer for timing elapsed V-EVENT to V-EVENT (V-V) intervals or A-EVENT to A-EVENT (A-A) intervals, escape interval timers for timing A-A, V-A, and/or V-V pacing escape intervals, an AV delay interval timer for timing an AV delays from a preceding A-EVENT (SAV) or A-TRIG (PAV), atrial and ventricular post-event timers for timing post-atrial and post-ventricular time periods, and an upper rate interval (URI) timer.

The post-event timers time out the post-ventricular time periods following a V-EVENT or a V-TRIG and post-atrial time periods following an A-EVENT or A-TRIG. The durations of the post-event time periods may also be selected as programmable parameters stored in the microcomputer 302. The post-ventricular time periods include the post-ventricular atrial refractory period (PVARP), a post-ventricular atrial blanking period (PVABP), a ventricular blanking period (VBP), and a ventricular refractory period (VRP). The post-atrial time periods include an atrial refractory period (ARP) during which an A-EVENT is ignored for the purpose of resetting the AV delay, and an atrial blanking period (ABP) during which atrial sensing is disabled. These post-atrial time periods time out concurrently with the time-out of the SAV or PAV delay started by an A-EVENT or an A-TRIG.

Microcomputer 302 controls the operational functions of digital controller/timer circuit 330, specifying which timing intervals are employed, and setting at least the programmed-in base timing intervals, via data and control bus 306. Digital controller/timer circuit 330 starts and times out these intervals and delays for controlling operation of the atrial and ventricular sense amplifiers in sense amplifiers circuit 360 and the atrial and ventricular pacing pulse generators in output amplifiers circuit 340.

The output amplifier circuit 340 contains atrial and ventricular pacing pulse generators corresponding to any of those presently employed in commercially marketed cardiac pacemakers providing atrial and ventricular pacing. In order to trigger generation of a V-PACE pulse, digital controller/timer circuit 330 generates a V-TRIG signal at the end of an AV delay provided by AV delay interval timer. Similarly, digital controller/timer circuit 330 generates an A-TRIG signal at the end of the V-A escape interval timed by an escape interval timer in order to trigger delivery of the A-PACE pulse. The output amplifiers circuit 340 includes switching circuits responsive to an A-PACE VS (vector select) command and a V-PACE VS command for coupling selected pace/sense electrode pairs from among the atrial and ventricular leads 14 and 16 and the IND_CAN electrode to the atrial and ventricular pulse generators so as to provide bipolar or unipolar atrial and/or ventricular pacing.

The sense amplifiers circuit 360 contains sense amplifiers corresponding to any of those presently employed in commercially marketed cardiac pacemakers for atrial and ventricular pacing and sensing. It has been common in the prior art to use very high impedance P-wave and R-wave sense amplifiers to amplify the voltage difference signal that is generated across the sense electrode pairs by the passage of a cardiac depolarization. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 330 provides programmed sensitivity commands to the sensitivity control register 350 that control sensitivity settings of the atrial and ventricular sense amplifiers 360.

A sense vector switch network 370 is interposed between the sense amplifiers circuit 360 and the atrial and ventricular lead conductors and the IND_CAN electrode. The switch network 370 responds to A-SENSE VS and V-SENSE VS vector select commands to configure the atrial and ventricular sense amplifiers for atrial and/or ventricular bipolar or unipolar sensing in the above described sense vectors. The sense amplifiers circuit 360 also includes blanking circuits for uncoupling the selected pairs of the lead conductors and the IND_CAN electrode from the inputs of the atrial and ventricular sense amplifiers during the ABP, PVABP and VBP before, during, and after delivery of a pacing pulse to any of the pace/sense electrode pairs to avoid saturation of the sense amplifiers.

If the IPG is programmed to a rate responsive mode, e.g. DDDR, DDIR, or VVIR, the signals output by one or more physiologic sensor are employed to provide pacing at a rate sufficient to meet the patient's need for cardiac output. Many physiologic sensors and/or signals have been employed in the prior art alone or in combination for measuring one or more rate control parameter (RCP) which directly or indirectly relate to metabolic requirements (e.g., demand for oxygenated blood). Such RCPs include, for example, QT interval evoked response, physical activity of the body, right ventricular blood pressure and the change of right ventricular blood pressure over time, venous blood temperature, venous blood oxygen saturation, respiration rate, minute ventilation, and various pre and post-systolic time intervals measured by impedance or pressure sensing within the right ventricle of the heart. Such RCP-measuring, sensor-driven pacemakers have been developed for the purpose of restoring rate response to exercise or other physiological stresses in patients lacking the ability to increase rate adequately by exertion. Any one or more of such RCPs and algorithms using the same to derive a pacing rate in the rate responsive pacing modes employed in the present invention can be employed.

For simplicity of discussion, in the exemplary IPG circuit 300, the RCP is the output signal of the patient activity sensor 316 processed in the patient activity sensor (PAS) circuit 322 to derive a physiologic escape interval and corresponding PAS_RATE. A timed interrupt, e.g., every two seconds, may be provided in order to allow the microprocessor 304 to analyze the output of the PAS circuit 322 and update the PAS_RATE defined V-A (or A-A or V-V) escape interval employed in the pacing cycle. The microprocessor 304 also optionally calculates AV delays, post-ventricular time periods, and post-atrial time periods that vary with the physiologic escape interval established in response to the RCP(s) and/or with the intrinsic atrial rate. The variable AV delays are usually derived as a fraction of a maximum AV delay set for the pacing lower rate (i.e., the longest escape interval).

Thus, FIG. 2 illustrates one common form of a dual chamber pacing IPG circuit 300 modified to perform the PTS algorithm of the present invention. The illustrated pacing system comprises two pacing channels, an atrial pacing channel comprising the atrial pacing pulse generator and atrial sense amplifier coupled to the selected electrodes as described above and a ventricular pacing channel comprising the ventricular pacing pulse generator and ventricular sense amplifier coupled to the selected electrodes as described above. The illustrated pacing system can be incorporated into a pacemaker as depicted in FIG. 1 or into an ICD. It will be understood that the present invention can also be incorporated in a single chamber pacing systems or in single and dual chamber, right and left heart chamber, pacing systems of the type disclosed in commonly assigned U.S. Pat. No. 6,456,878 issued to Yerich et al. for CHF patients.

Figure 3:
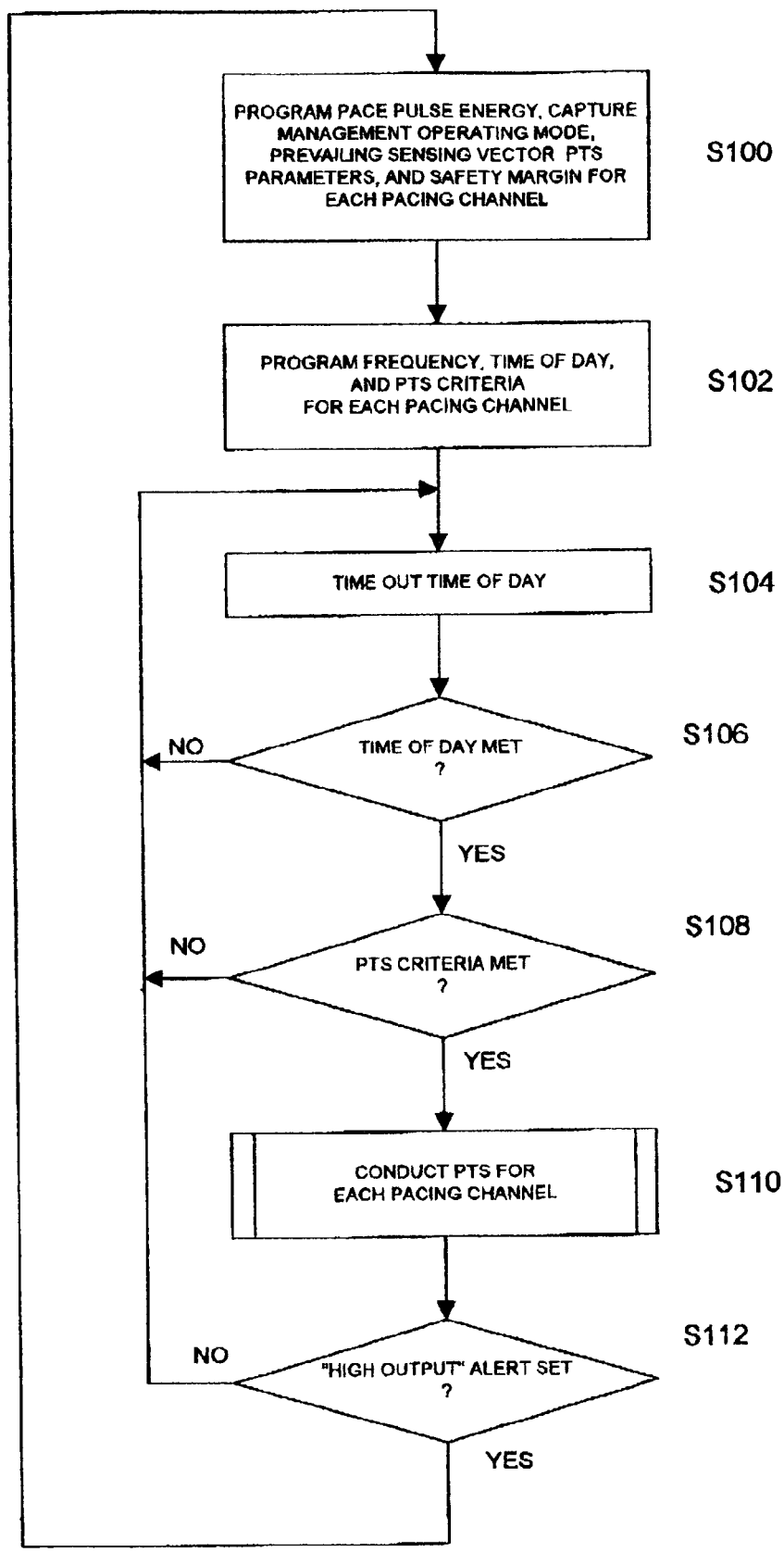
FIG. 3 is a high level flow diagram of the steps of setting up and practicing the Capture Management algorithm of the present invention.

Turning now to FIG. 3, the Capture Management algorithm is programmed in step S100 to periodically perform the PTS in the atrial and/or ventricular pacing channels to either simply monitor the pacing thresholds or to adjust the pacing energy to provide the appropriate safety margin above the LOC energy level in the Adaptive mode automatically when certain conditions are present. If Adaptive mode is selected, then the physician must also select the prevailing sense vector to use for sensing the evoked response. For the sake of simplicity, FIG. 3 will assume that the pacing IPG has been programmed to switch the sense amplifier if noise is detected.

The physician schedules the PTS in step S102 to start at a prescribed time and defines PTS criteria that have to be met to enable running of the PTS. Nominally, PTS is scheduled to operate once a day while the patient is at rest. This usually means that a PTS teat will be performed at night while the patient is asleep. The time of day is timed out in step S104. When the time of day occurs in step S106, the Capture Management algorithm first determines whether other patient and device criteria are met in step S108. One patient criteria is whether the patient is active or inactive which can be determined from the output of the PAS circuit 322 and/or the patient's heart rate. The PTS results are more reliable when the patient is at rest and the patient's rate is, in general, less than 100 ppm. In addition, the Capture Management algorithm determines in step S108 whether other competing operations of the pacing IPG are functioning, such as mode switching or rate drop response, among others. These are detailed further in the Kappa® 900/800 *Series Pacemaker Reference Guide*.

Figure 4:
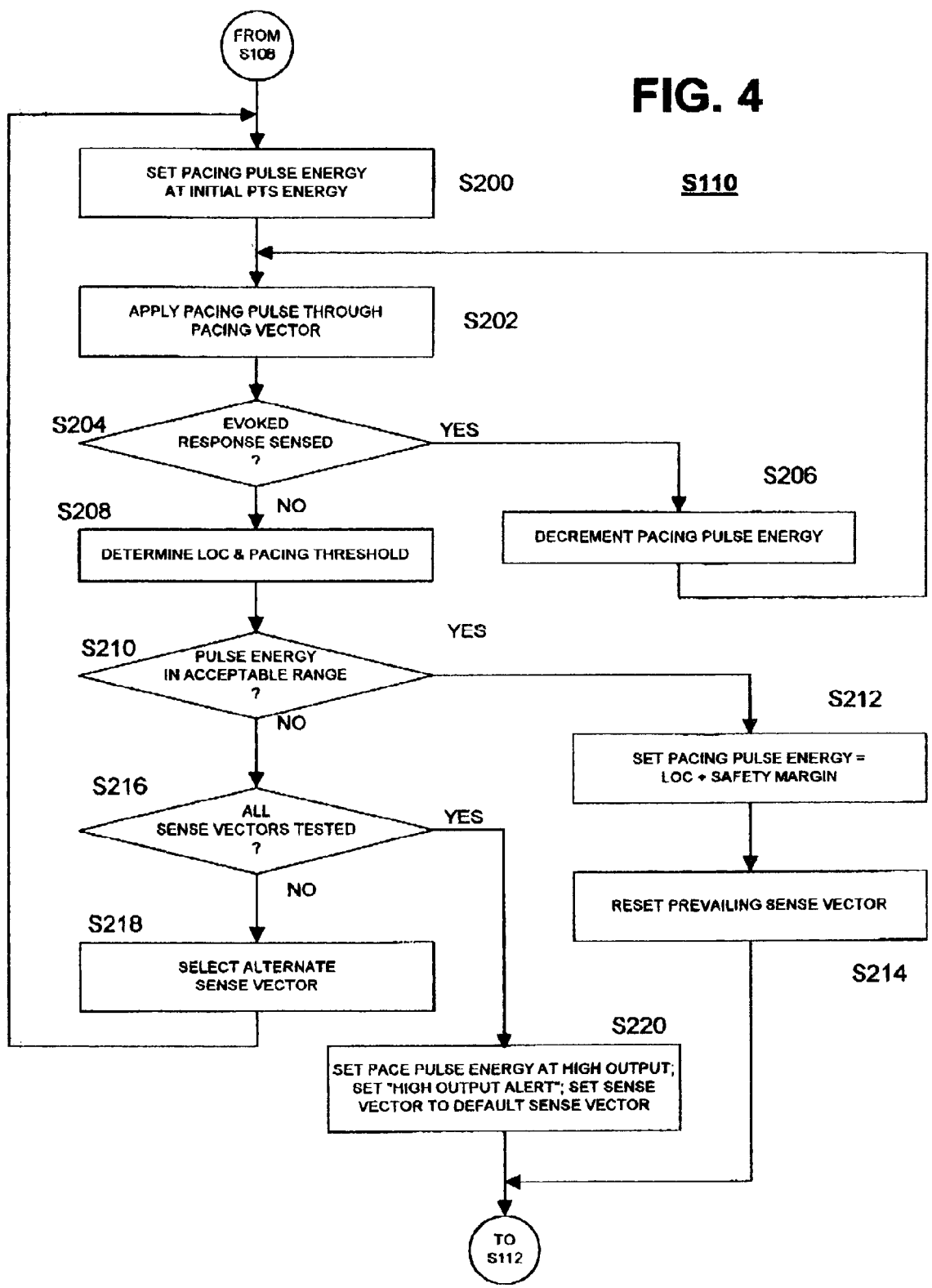
FIG. 4 is a flow chart of steps of performing the PTS employing multiple sense vectors to minimize undersensing in accordance with the present invention.

The PTS is conducted in step S110 depicted in greater detail in FIG. 4 if the PTS criteria are satisfied in step S108. The PTS involves adjusting the pacing pulse energy and determining if capture is sensed at that energy in accordance with any of the known stimulation threshold methods. For example, when the ventricular pacing channel is tested, the pacing pulses are delivered in 3 cycles each of which comprise 3 ventricular events that may be paced or sensed events. If a paced event is counted, the V-PACE pulse is at the programmed amplitude and width. A test pace follows each support cycle at the decremented V-PACE test pulse amplitude and width. A backup V-PACE pulse, at the programmed pulse amplitude and a width of 1.0 ms, is delivered 110 ms after the test V-PACE pulse as is conventional in the art.

The test pace pulse energy is automatically incremented or decremented depending on where the PTS is in its total cycle. Since it is necessary to perform the rheobase test first, the pacing pulse amplitude is decremented at a given test pulse width. For example, the test pulse width is 0.4 ms. Thus, the pulse amplitude is decreased at this pulse width until LOC occurs. Then, the amplitude is increased until capture is regained. The amplitude at which capture is regained (the "rheobase" threshold) is used as a benchmark pulse amplitude to use during the chronaxie test for LOC and recapture. The pulse amplitude is doubled from the rheobase while the pulse width is decremented to lose capture and incremented to regain capture. The algorithm again uses the support cycle method, that is, three cycles of three pace or sense events followed by a test pace whose pulse width is either the one programmed or the one that the previous PTS established as valid. Thus, the pulse width is decreased from a known value until LOC occurs, and then increased until capture is again attained to determine the "chronaxie" threshold. (See FIG. 5 for further details of this operation.)

While this process seems straightforward, lead polarization, that is, the dissipation of electrical "noise" at the electrode-tissue interface during and after the pacing pulse is a constant and well-documented obstacle to achieving suitable sensing of the evoked response. At times, the noise "obliterates" the evoked response signal, that is, the ability to sense the evoked response. Additionally, the amplitude of the evoked response may be quite low as compared to the pacing output pulse. Moreover, it sometimes occurs that the evoked response falls within the blanking period due to short tip-to-ring spacing on a bipolar lead. In both of these latter two cases, the sense amplifier cannot detect the evoked response. The inability to sense the evoked response is termed undersensing. Preventing undersensing of the evoked response 110 is the subject of the present invention. How this occurs will be clarified in FIGS. 4-6 and the following discussion. Briefly stated, if the sense amplifier cannot detect the evoked response while in the prevailing sense vector (e.g., a bipolar sense vector) that has prevailed since the preceding PTS was conducted, the sense amplifier is switched to sense in another sense vector, (e.g., a unipolar sense vector) and repeats the PTS. If noise is also present in the unipolar sense vector, the sense amplifier will switch back to the bipolar sense vector.

Once a suitable measurement of the rheobase and chronaxie thresholds are made, these data are used to adjust the output amplitude and pulse width automatically. Such adjustment includes a safety factor previously determined by the physician, such as, a 2× or 1.5× factor above the rheobase value determined during the PTS.

Turning to FIG. 4, it illustrates the performance of the PTS for each pacing channel pursuant to step S110 of FIG. 3 first testing the prevailing sense vector established during programming or a preceding scheduled PTS and then, if necessary, testing the alternate sense vector or vectors that are available in the pacing channel. If the PTS of the prevailing sense vector is successful, then the pacing pulse energy is reset to reflect the determined pacing threshold and sensing continues using the electrodes defining the prevailing sense vector for the pacing channel until the next scheduled PTS is undertaken per steps S104-S108. If the PTS of the prevailing sense vector is unsuccessful, then the sense vector is changed and the PTS steps are repeated using the changed sense vector. If the PTS of the changed sense vector is successful, then the pacing pulse energy is reset to reflect the determined pacing threshold and sensing continues using the electrodes defining the changed sense threshold for the pacing channel as the new prevailing sense vector until the next scheduled PTS is undertaken per steps S104-S108. If the PTS of the changed sense vector is unsuccessful, then the sense vector is set to a default sense vector that can be programmed or may be set by the algorithm, the "high output" alert is set, and the pacing pulse energy is set to the high output.

One conventional form of a rheobase and chronaxie threshold test is depicted in steps S200-S212, but it will be understood that the test steps may take any of the known forms. Steps S214, S216 and S218 operating in conjunction with steps S200-S212 and S220 reflect how undersensing can be minimized in accordance with the invention by repeating the PTS for alternate sense vectors if a "high output" is declared in the PTS of the prevailing sense vector.

Thus, the PTS is first run with the sense amplifier of the pacing channel coupled to the pace/sense electrodes defining the prevailing sense vector. For simplicity, it will be assumed that the pacing pulse energy (pulse width or pulse amplitude) of the PTS pacing pulse in the series of 3 pace or sense events is decremented from an initial PTS pulse energy in step S200. The PTS pacing pulse is delivered through the pace vector of the pacing channel in step S202. If the evoked response is sensed in step S204, then the pacing pulse energy is decremented in step S206. Steps S202, S204 and S206 are repeated until evoked response is not sensed in step S204. The pulse energy is incremented and retested for evoked response in step S208 to determine the actual pace pulse energy threshold. These steps are repeated to determine rheobase and chronaxie thresholds as described above.

If the pulse energy determined in step S208 is in an acceptable range as determined in step S210, then the pacing pulse energy is reset to reflect the pulse energy at LOC (or the determined threshold) plus a safety margin in step S212 in the known manner. In this case, the prevailing sense vector is unchanged in step S214 and the PTS is concluded returning to step S112 of FIG. 3.

If the pulse energy determined in step S208 is not in the acceptable range as determined in step S210, then an alternate sense vector is selected in step S218 if one is determined to be untested in step S216. Since there are more than one possible unipolar sense vector, it would be possible to program the Capture Management algorithm to repeat the PTS in one or more of the alternate unipolar sense vector. The "high output" alert may be flagged for confirmation or refutation depending upon whether or not the PTS using the alternate sense vector is able to confirm or refute it.

For example, the PTS of the ventricular sense amplifier operating in a bipolar sensing mode using the ring and tip electrodes 28 and 30 may have resulted in a failure to sense an evoked response at any pacing pulse energy or within the acceptable pulse energy range determined in step S208. An alternate V-SENSE VS is applied in step S218 to sense vector switch network 370 of FIG. 2 to select one of the possible unipolar sense vectors described above. Then, the steps S200-S216 are repeated to determine if an evoked response can be sensed in the alternate ventricular sense vector at an acceptable pulse energy.

If ventricular pacing threshold can be determined following steps S202-S210, then the pacing pulse energy is reset to reflect the pulse energy at LOC (or the determined threshold) plus a safety margin in step S212 in the known manner. In this case, the prevailing sense vector is changed in step S214 and the PTS is concluded returning to step S112 of FIG. 3. Thus, in this example, the new prevailing ventricular sense vector is the tested unipolar sense vector.

However, if a ventricular pacing threshold cannot be determined following steps S202-S210 using the tested unipolar sense vector, then the V-PACE pulse energy is set to maximum or high output, the "high output" flag or alert is stored, and the ventricular sense vector is set to a default sense vector. In this example, the default sense vector may be the bipolar ventricular sense vector prevailing when the PTS was initiated.

Taking this example further, the same steps are followed if the prevailing ventricular sense vector is a unipolar ventricular sense vector. The alternate sense vectors can include the other possible unipolar ventricular sense vectors as well as the bipolar ventricular sense vector.

Figure 5:
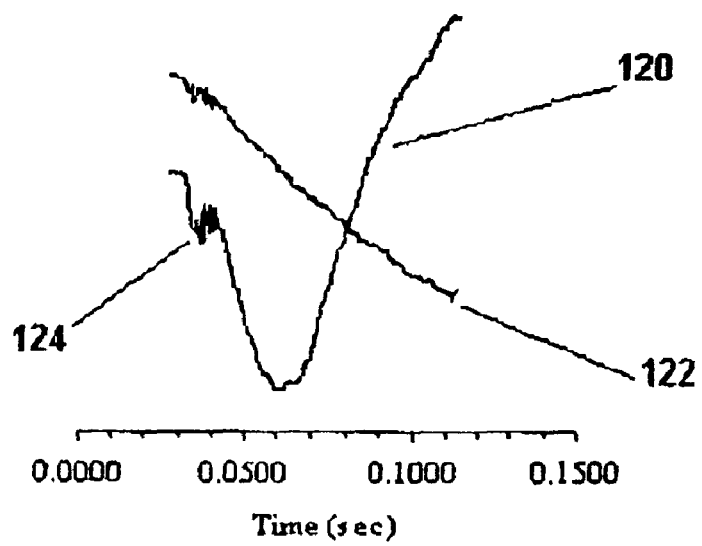
FIG. 5 is an illustration of one embodiment of how a sense amplifier detects the presence of the slew rate of an evoked response.
Figure 6:
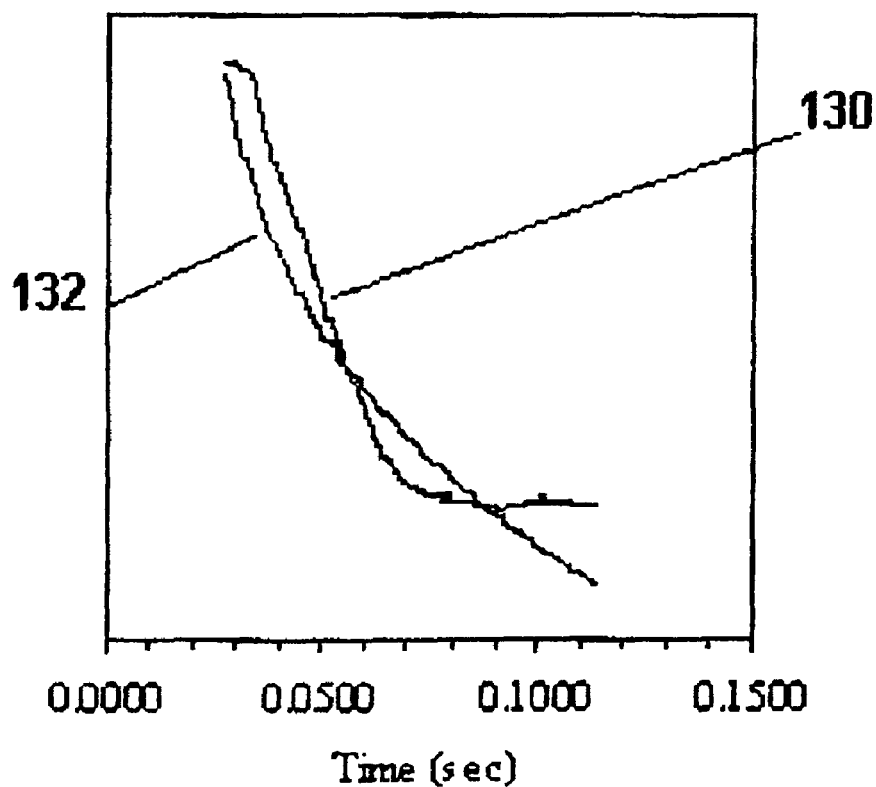
FIG. 6 is an illustration of a second embodiment of how a sense amplifier detects the presence of the slew rate of an evoked response.

The above described steps are applicable to the PTS of the atrial pacing channel and can applied to left heart pacing channels of a right and left heart chamber pacing system, Turning to sensing issues, in both FIGS. 5 and 6, it is important that the sense amplifier be able to distinguish between the evoked response and LOC. Thus, the sense amplifier cannot be overwhelmed with noise that would result in a negative detection. Noise, from whatever source, can make it impossible to detect capture or LOC. At times, the amplitude of the evoked response signal, as compared to the pacing pulse, may be so small that it is unable to be detected. Alternatively, the evoked response signal may falls into the blanking period that follows the pacing pulse due to short tip-to-ring spacing on a bipolar lead. The present invention changes the polarity of the sense amplifier to "improve" its sensitivity when either or both of these issues are suspected to be present.

In is original implementation in the Medtronic® Kappa® 700 device, the sense amplifier would automatically distinguish between a low polarization and high polarization lead. If a low polarization lead was in use, the sense amplifier looked only at the change in sign of the slew rate, as depicted in FIG. 5. If, on the other hand, a high polarization lead were in use, the sense amplifier would look for a sharp drop in sign, as depicted in FIG. 6. In either case, however, if the signal-to-noise level did not allow the sense amplifier to detect either type of change in the slew rate, the device would identify the operation as LOC. If such LOC continued to occur, the pacing pulse amplitude would have been switched to 5 volts; otherwise a high threshold would be measured. The setting of 5 volts would remain until either a subsequent PTS would detect a lower threshold or until the next follow-up when the physician would try to "troubleshoot" the problem and, if possible, correct it. It is this situation that the present invention corrects. With this background in mind, FIGS. 5 and 6 will make it clear to those familiar with the art why the present invention improves the implementation already in place.

FIG. 5 is displays of how the sense amplifier detects the presence of the slew rate of an evoked response when the device is connected to a low polarization lead. Determining capture after a pacing pulse requires recognition of the ventricular evoked response. The major deterrent to this recognition is electrical noise 124 such as that produced by lead polarization, that is, the dissipation of energy at the electrode-tissue interface during and after the pacing pulse. To gain such recognition, the standard sense amplifier circuitry was altered to ensure that the it can discriminate between the evoked response, LOC, and lead polarization. First, the circuitry was made responsive to the change in sign/direction of the slew rate 120. The slew rate signal for LOC 122 is always negative/downward, whereas the slew rate for capture 120 changes sign/direction.

In FIG. 5, the noise level 124 is quite low. In this instance, the present invention would not switch the sense amplifier's polarity. Assuming that the sense amplifier is coupled to a bipolar electrode pair, that is, in its nominal state, then no change would be made. But, if the polarity had been switched to the unipolar sense vector from the nominal bipolar sense vector due to a large noise signal, then the sense amplifier would remain using the unipolar sense vector.

FIG. 6 shows that the sense amplifier was made more sensitive to the increase in magnitude of the slew rate to accommodate the requirements of a high polarization lead. Capture 130, i.e., an evoked response, is displayed as a sharper drop that starts to occur at about 40 ms. This sharper drop is the sign of capture as opposed to the less precipitous drop that shows LOC 132.

All patents and publications referenced herein are incorporated by reference in their entireties.

The preceding specific embodiments are illustrative of the practice of the invention. It is to be understood, therefore, that other expedients known to those of skill in the art or disclosed herein may be employed without departing from the invention or the scope of the appended claims. It is therefore to be understood that the invention may be practiced otherwise than is specifically described, without departing from the scope of the present invention. As to every element, it may be replaced by any one of infinite equivalent alternatives, only some of which are disclosed in the specification.

What is claimed is:

1. In a pacing system, wherein a pace pulse generator is selectively coupled to an active pace/sense electrode adapted to be placed in operative relation to a heart chamber and to one of an indifferent pace/sense electrode proximate to the active pace/sense electrode to deliver pace pulses to the heart chamber in a bipolar pace vector or a remote indifferent pace/sense electrode to deliver pace pulses to the heart chamber in a unipolar pace vector, and a sense amplifier coupled to the active pace/sense electrode and selectively coupled, to provide a prevailing sense vector, to one of the indifferent pace/sense electrode proximate to the active pace/sense electrode whereby the prevailing sense vector is a bipolar sense vector or to the remote indifferent pace/sense electrode whereby the prevailing sense vector is a unipolar sense vector, a method of periodically conducting a pacing threshold search in a pacing channel including the sense amplifier and the pace pulse generator coupled with the active and indifferent pace/sense electrodes, the pacing system including a predetermined value set for a high output pace pulse energy to be utilized when a high energy output pacing condition is detected, the method comprising:

(a) triggering the commencement of the pacing threshold search;

(b) conducting the pacing threshold search employing the sense amplifier sensing in the prevailing sense vector to determine if a stimulation energy threshold determined in the prevailing sense vector requires setting the pace pulse energy to the high output pace pulse energy to reliably capture the heart chamber;

(c) if the high output pace pulse energy is determined to be required, selectively coupling the sense amplifier to an alternate one of the indifferent pace/sense electrodes to sense in the other one of the bipolar sense vector or unipolar sense vector as an alternate sense vector;

(d) repeating step (b) to determine if the stimulation energy threshold determined in the alternate sense vector requires setting the pace pulse energy to a high output pace pulse energy to reliably capture the heart chamber; and (e) if the high output pace pulse energy is determined to be required in step (d), setting the prevailing sense vector to a default one of the bipolar or unipolar sense vectors and the pace pulse energy to the high output pace pulse energy and thereafter retriggering the pacing threshold search employing the default one of the vectors.

2. The method of claim 1, further comprising:

(f) if the high output pace pulse energy is determined to not be required in step (d), setting the prevailing sense vector to the alternate sense vector, whereby the alternate sense vector becomes the prevailing sense vector when the pacing threshold search is again triggered, and determining a pace pulse energy sufficient to capture the heart chamber.

3. In a pacing system, wherein a pace pulse generator is selectively coupled to an active pace/sense electrode adapted to be placed in operative relation to a heart chamber and to one of an indifferent pace/sense electrode proximate to the active pace/sense electrode to deliver pace pulses to the heart chamber in a bipolar pace vector or a remote indifferent pace/sense electrode to deliver pace pulses to the heart chamber in a unipolar pace vector, and a sense amplifier coupled to the active pace/sense electrode and selectively coupled, to provide a prevailing sense vector, to one of the indifferent pace/sense electrode proximate to the active pace/sense electrode whereby the prevailing sense vector is a bipolar sense vector or to the remote indifferent pace/sense electrode whereby the prevailing sense vector is a unipolar sense vector, apparatus for periodically conducting a pacing threshold search in a pacing channel comprising the sense amplifier and the pace pulse generator coupled with the active and indifferent pace/sense electrodes, the pacing system including a predetermined value set for a high output pace pulse energy to be utilized when a high energy output pacing condition is detected, the system comprising:

- timing means for triggering the commencement of the pacing threshold search;
- means for conducting the pacing threshold search to determine if a stimulation energy threshold determined in the prevailing sense vector requires setting the pace pulse energy to the high output pace pulse energy to reliably capture the heart chamber;
- means operable if the high output pace pulse energy is determined to be required for selectively coupling the sense amplifier to an alternate one of the indifferent pace/sense electrodes in the other one of the bipolar sense vector or unipolar sense vector to thereby sense in an alternate sense vector;
- means for again conducting the pacing threshold search to determine if the stimulation energy threshold determined in the alternate sense vector requires setting the pace pulse energy to a high output pace pulse energy to reliably capture the heart chamber; and
- means for setting the prevailing sense vector to a default one of the bipolar or unipolar sense vectors and the pace pulse energy to the high output pace pulse energy if the high output pace pulse energy is again determined to be required and for subsequently conducting the pacing threshold using the default one of the sense vectors.

4. The apparatus of claim 3, wherein said setting means is operable if the high output pace pulse energy is determined to not be required for setting the prevailing sense vector to the alternate sense vector, whereby the alternate sense vector becomes the prevailing sense vector when the pacing threshold search is again triggered, and determining a pace pulse energy sufficient to capture the heart chamber.

5. A pacing system comprising a pace pulse generator, a plurality of active pace/sense electrodes coupled to said generator and adapted to be placed in operative relation to a heart chamber, and a sense amplifier coupled with said plurality of electrodes and operable to sense capture detection using alternate sensing vectors, said pacing system further comprising:

(a) means for triggering the commencement of a pacing threshold search;
(b) means for conducting the pacing threshold search employing the sense amplifier to sense capture detection using a first of the sensing vectors;
(c) wherein the search conducting means is responsive to the pacing threshold search using the first sensing vector indicating that an unacceptably pacing pulse high energy level is required to capture the heart chamber, and subsequently conducts the pacing threshold search employing the sense amplifier to sense capture detection using a second one of the sensing vectors; and
(d) wherein the search conducting means is responsive to pacing threshold searches using all of the alternate sensing vectors indicating that an unacceptably pacing pulse high energy level is required to capture the heart chamber, and subsequently conducts the pacing threshold search employing the sense amplifier to sense capture detection using a predefined default one of one of the sensing vectors.

6. The system of claim 5, wherein the search conducting means is responsive to the pacing threshold search using the first sensing vector indicating that an acceptable pacing pulse high energy level is required to capture the heart chamber, and subsequently conducts the pacing threshold search employing the sense amplifier to sense capture detection using the second one of the sensing vectors.

7. In a pacing system comprising a pace pulse generator, a plurality of active pace/sense electrodes coupled to and adapted to be placed in operative relation to a heart chamber, and a sense amplifier coupled with said plurality of electrodes to sense capture detection using alternate sensing vectors, a method comprising:

(a) triggering the commencement of a pacing threshold search;
(b) conducting the pacing threshold search employing the sense amplifier to sense capture detection using a first of the sensing vectors;
(c) if the pacing threshold search using the first sensing vector indicates that an unacceptably pacing pulse high energy level is required to capture the heart chamber, subsequently conducting the pacing threshold search employing the sense amplifier to sense capture detection using an a second one of the sensing vectors;
(d) If pacing threshold searches using all alternate sensing vectors indicate that an unacceptably pacing pulse high energy level is required to capture the heart chamber, subsequently conducting the pacing threshold search employing the sense amplifier to sense capture detection using a predefined default one of one of the sensing vectors.

8. The method of claim 7, further comprising:
(e) If the pacing threshold search using the first sensing vector indicates that an acceptable pacing pulse high energy level is required to capture the heart chamber, subsequently conducting the pacing threshold search employing the sense amplifier to sense capture detection using the second one of the sensing vectors.

* * * * *